US00PP15068P2

(12) United States Plant Patent
Mowrey et al.

(10) Patent No.: US PP15,068 P2
(45) Date of Patent: Aug. 3, 2004

(54) PLUM TREE NAMED 'SUPLUMTHIRTYTHREE'

(50) Latin Name: *Prunus salicina*
Varietal Denomination: Suplumthirtythree

(75) Inventors: Bruce D. Mowrey, Watsonville, CA (US); Terry A. Bacon, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/463,792

(22) Filed: Jun. 16, 2003

(51) Int. Cl.[7] ..... A01H 5/00

(52) U.S. Cl. ..... Plt./184

(58) Field of Search ..... Plt./184

(56) References Cited

U.S. PATENT DOCUMENTS

PP2,747 P 6/1967 Garabedian

*Primary Examiner*—Bruce R. Campell
*Assistant Examiner*—W C Haas
(74) *Attorney, Agent, or Firm*—Knobbe Martens Olson & Bear, LLP

(57) ABSTRACT

A new and distinct plum variety that possesses heavy and consistent production of very large, smooth, red-skinned fruit having a juicy flesh that becomes pink colored as the fruit ripens.

1 Drawing Sheet

Latin name of the genus and species of the plant claimed: *Prunus salicina.*
Variety denomination: 'Suplumthirtythree'.

BACKGROUND AND SUMMARY OF THE INVENTION

The present invention relates to the discovery and asexual propagation of a new and distinct cultivar of Plum Tree, herein after referred to by the cultivar name 'Suplumthirtythree'. The new variety originated by hybridization performed by Bruce Mowrey. The new variety was first evaluated by Terry Bacon on Sun World Experimental Ranch 75 near Wasco, Calif. in Kern County. The new variety 'Suplumthirtythree' is characterized by heavy and consistent production of very large (average 70 mm diameter), smooth, red-skinned fruit. The fruit flesh is juicy and sweet (17° brix) and becomes pink colored as the fruit ripens. The fruit ripens during the first half of August in the Bakersfield, Calif. area.

The parent varieties were first crossed in 1994, with the date of planting of February 1995, and the date of first flowering being March 1997. The new plum variety was first asexually propagated by Terry Bacon near Wasco, Kern County, Calif. in May 2001, by grafting onto Nemaguard rootstock.

The seed parent is Sun World breeding selection, '90P-068' (unpatented) that was selected from the progeny of a cross between 'Midsummer' (unpatented) crossed with pollen from Sun World breeding selection, '295-198' (unpatented). 'Suplumthirtythree' is distinguished from its seed parent by ripening 15 days earlier with fruit diameter that averages 70 mm as compared to 61 mm of the seed parent.

The pollen parent is Sun World breeding selection, '90P-064' (unpatented) that was selected from the progeny of a cross between 'Suplumsix' (U.S. Plant Pat. No. 2,747) crossed with pollen from 'Suplumeleven' (U.S. Plant Pat. No. 4,902). 'Suplumthirtythree' is distinguished from its pollen parent by ripening 7 days later with fruit diameter that averages 70 mm as compared to 61 mm of the pollen parent.

The new variety most nearly resembles 'Fortune' (unpatented) plum variety. It may be distinguished by ripening 30 days later with fruit diameter that averages 70 mm compared with 64 mm diameter for 'Fortune'.

The new plum tree variety cv. 'Suplumthirtythree' has been shown to maintain its distinguishing characteristics.

BRIEF DESCRIPTION OF THE FIGURE

The accompanying color photographic illustration in FIG. 1 shows typical specimens of the foliage and fruit of the present new plum variety. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED BOTANICAL DESCRIPTION OF THE INVENTION

Figure 1:
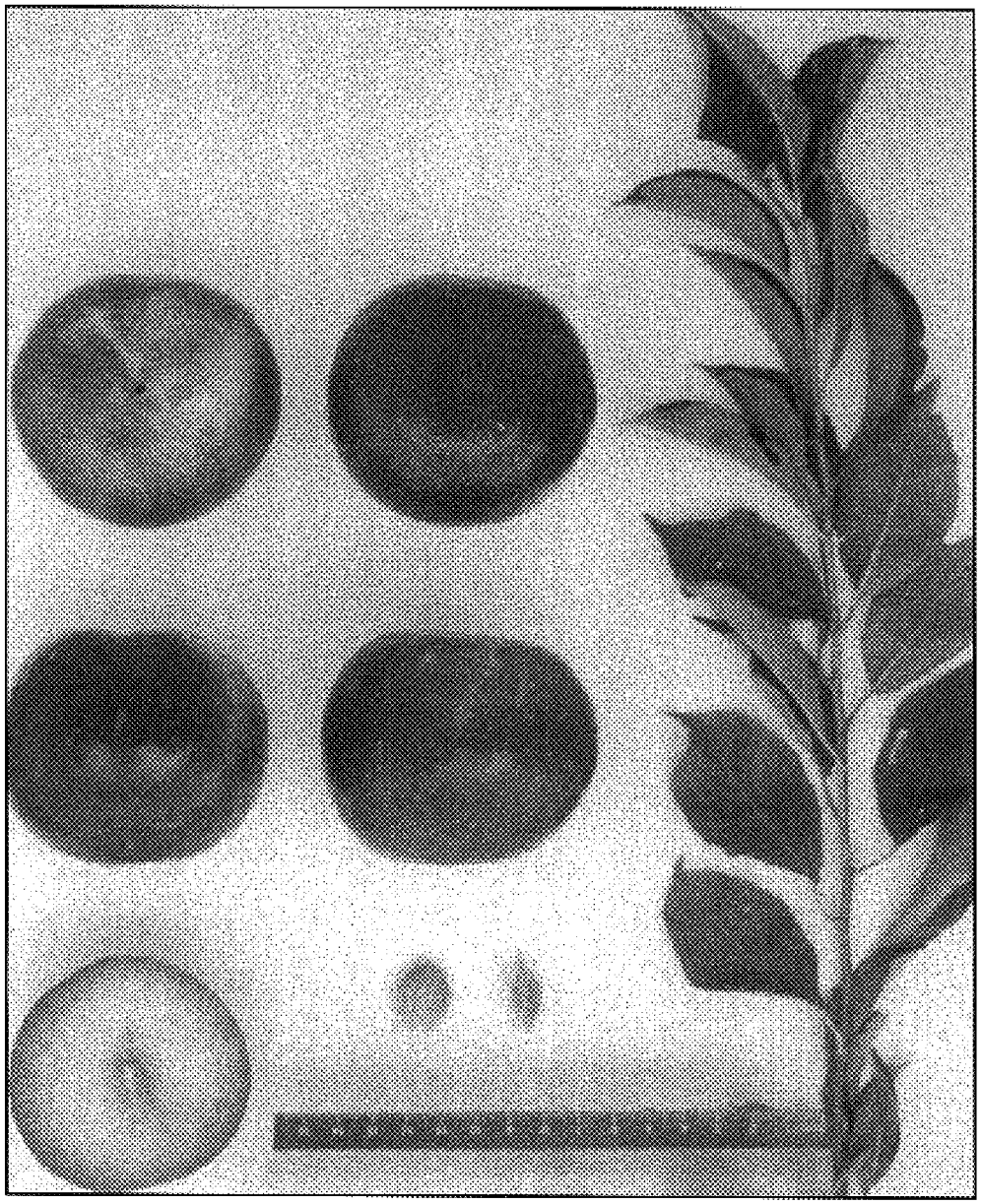

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

The descriptive matter which follows pertains to 7 year old trees grown in the vicinity of Wasco, Kern County, Calif., during 2002, and is believed to apply to plants of the variety grown under similar conditions of soil and climate elsewhere.

TREE (Measurements Taken on a 7 Year Old Tree)

General:
- *Size.*—Medium, normal for most plum varieties.
- *Height.*—Reaches a height of approximately 3–4 meters including normal pruning.
- *Vigor.*—Vigorous, growth of approximately 1.8 to 2 meters height the first growing season.
- *Growth.*—Upright-spreading.
- *Productivity.*—Productive. Fruit set is usually two or more times desired amount for marketable size fruit. Thinning and spacing of fruit is necessary.
- *Form.*—Vase formed.
- *Fruit bearing.*—Regular. No alternate bearing observed.
- *Fertility.*—Somewhat self-fertile but a pollinator variety improves set.
- *Density of foliage.*—Medium-dense. Pruning is required to open tree vase shape, allowing more sunlight to center of tree.
- *Hardiness.*—Hardy in all fruit growing areas of California.
- *Winter chilling requirement.*—Approximately 750 hours at or below about 7.2° C.
- *Tree resistance/susceptibility.*—No specific testing for relative plant disease resistance/susceptibility has been designed. Under close observation on Sun World Ranch 75 near Wasco, Calif., no particular plant/fruit disease resistance/susceptibility has been observed.
- *Root stock.*—Nemaguard.

Trunk: (Measurements at 30 cm above soil line).
- *Diameter.*—Approximately 14 cm. Varies with soil type, fertility, climatic conditions and cultural practices.
- *Surface texture.*—Medium shaggy, increases with age of tree.
- *Color.*—About Greyed-orange 165B in bark recesses to Greyed-green 198B on exposed surfaces, becomes darker with age.

Branches: (Measurements at 90 cm above soil line).
- *Diameter.*—Ranges from approximately 7 to approximately 9 cm.
- *Surface texture.*—Smooth on 1st year wood, increasing roughness with tree age.
- *Color.*—About Greyed-orange 165B in bark recesses, to about Greyed-green 198B on exposed surfaces.

Branch lenticels:
- *Number.*—Few.
- *Length.*—Approximately 3 mm.
- *Width.*—Approximately 2 mm.
- *Color.*—About Greyed-orange 165B.

LEAVES (Data Taken in July on Fully Expanded Leaf at Midpoint of Current-Season Growth)

General:
- *Average length.*—Approximately 80 mm.
- *Average width.*—Approximately 35 mm.
- *Form.*—Broadly elliptic.
- *Leaf blade tip.*—Cuspidate.
- *Leaf base.*—Cuneate.
- *Margin.* —Slightly crenate.
- *Venation.*—Pinnately net veined.
- *Thickness.*—Medium.
- *Color of upper surface.*—About Yellow-green 147A.
- *Color of lower surface.*—About Yellow-green 148D.
- *Surface texture.*—Smooth.

Petiole:
- *Length.*—Approximately 10 mm.
- *Diameter.*—Approximately 1.5 mm.
- *Color.*—About Yellow-green 144C with highlights of about Red 40B where exposed to sunlight.

Glands:
- *Average number.*—Varies from approximately 2 to 3.
- *Positioning.*—Alternate on upper portion of petiole and base of leaf blade.
- *Size.*—Approximately 0.4 mm by approximately 0.4 mm.
- *Shape.*—Globose.
- *Color.*—About Greyed-yellow 160A.

Stipules:
- *Number of stipules per bud.*—Approximately two.
- *Length.*—Approximately 4 to 5 mm.

FLOWERING SHOOTS (Data Taken in July at Midpoint of Current-Season Growth)

- *Diameter.*—Approximately 5 mm.
- *Color.*—About Greyed-orange 164B, with slight green background.

Flowering shoot leaf buds:
- *Shape.*—Ovoid.
- *Length.*—Approximately 2 mm.
- *Width.*—Approximately 1 mm.
- *Color.*—About Greyed-orange 165A.

Flowering shoot flower buds:
- *Number per node.*—Usually 2, up to 4.
- *Shape.*—Ovoid.
- *Length.*—Approximately 1.2 mm.
- *Width.*—Approximately 1 mm.
- *Color.*—About Greyed-orange 165A.

FLOWERS

General:
- *Date of first bloom.*—Mar. 1, 2002.
- *Date of full bloom.*—Mar. 6, 2002.
- *Size (diameter of the fully open flower).*—Approximately 23 mm.
- *Flower aroma.*—Very slight.

Peduncle:
- *Length.*—Approximately 7 mm.
- *Diameter.*—Approximately 1 mm.
- *Color.*—About Yellow-green 145A.

Petals:
- *Number per flower.*—5.
- *Arrangement.*—Overlapping.
- *Length.*—Approximately 10 mm.
- *Width.*—Approximately 8 mm.
- *Shape.*—Circular.
- *Apex shape.*—Rounded.
- *Base shape.*—Narrows at point of attachment.
- *Color (fully opened flower).*—White.
- *Surface texture.*—Smooth.
- *Margins.*—Smooth.

Sepals:
- *Number per flower.*—5.
- *Length.*—Approximately 3 mm.

*Width.*—Approximately 3 mm.
*Shape.*—Obovate with rounded apex.
*Color.*—About Yellow-green 144C.
*Surface texture.*—Rippled.

Stamens:
*Number per flower.*—Approximately 28 (ranges from approximately 22 to 32).
*Length.*—Approximately 7 mm.
*Filament color.*—White.
*Anther color* (*just before dehiscence*).—About Yellow-orange 20A.
*Pollen color.*—About Greyed-orange 168A.

Pistil:
*Number of pistils per typical flower.*—Usually one.
*Frequency of supplementary pistils.*—Occasionally two.
*Pistil length.*—Approximately 9 mm.
*Pubescence.*—None.
*Ovary diameter.*—Approximately 1 mm.
*Stigma position in relation to anthers.*—Stigma extends slightly below anthers.

FRUIT (Data Taken at Firm-Ripe Stage on Mature Tree Managed to Obtain Maximum Quality Under Conditions Stated Above)

General:
*Harvest data of first pick.*—Aug. 1, 2002.
*Harvest date of last pick.*—Aug. 12, 2002.
*Length* (*stem end to apex*).—Approximately 65 mm.
*Diameter in line with suture plane.*—Approximately 70 mm.
*Diameter perpendicular to suture plane.*—Approximately 70 mm.
*Average weight.*—Approximately 215 gm.
*Shape viewed from apex.*—Rounded, nearly symmetrical.
*Shape viewed from side, facing suture.*—Rounded, nearly symmetrical.
*Shape viewed from side, perpendicular to suture.*—Rounded, nearly symmetrical.
*Fruit apex shape.*—Rounded to slightly flattened.
*Fruit stem-end cavity depth.*—Shallow.

Stem:
*Length.*—Approximately 7 mm.
*Diameter.*—Approximately 2 mm.
*Color.*—About Green 143C.

Skin:
*Thickness.*—Medium.
*Adherence to flesh.*—Tenacious.
*Surface texture.*—Smooth.
*Pubescence.*—None.
*Bloom.*—Moderate amount.
*Ground color.*—Showing on fruit shoulders, about Yellow-green 150C, becoming about Yellow 10C.
*Overcolor.*—About Red 45A covering most of the fruit except some areas of the stem-end.
*Taste.*—Acidic.

Flesh:
*Color.*—About Red 36D, becoming about Red 43B from perimeter and pit cavity, toward mid section as fruit matures.
*Texture.*—Fine, firm.
*Ripens.*—Evenly.
*Fibers.*—Few.
*Flavor.*—Sweet-tart to sweet-mild.
*Aroma.*—Slight.
*Brix.*—Approximately 17 degrees.
*Juice.*—Plentiful.
*Use.*—Dessert. Market, local and long distance.
*Keeping and shipping quality.*—Good. Holds well in cold storage for Approximately 6 weeks and maintains good firmness and eating quality. Minimal bruising and scarring in packing and shipping trials.

STONE (Measurements Taken on Dried Stones)

General:
*Adherence to flesh.*—Semi-freestone.
*Length.*—Approximately 24 mm.
*Diameter in line with suture plane.*—Approximately 16 mm.
*Diameter perpendicular to suture plane.*—Approximately 9 mm.
*Form* (*viewed from broad side*).—Eliptical oblong, slightly asymmetrical.
*Form* (*viewed from stem end*).—Oval, symmetrical.
*Base shape.*—Flattened, retuse at stem attachment.
*Apex shape.*—Acuminate with a small, sharp point.
*Stone surface.*—Irregularly furrowed throughout. Heavily ridged toward base. Lightly pitted throughout.
*Comparison of stone halves.*—Equal.
*Ridges.*—1 on each side of the suture. Well-formed and beginning at the base and extending throughout the length of the stone.
*Stone outgrowing keel.*—Well developed.
*Tendency to split.*—None.
*Stone color when dried.*—About Greyed-yellow 161A.

What is claimed is:

1. A new and distinct plum tree named 'Suplumthirtythree' as herein described and illustrated.

* * * * *